(12) United States Patent
Bakker et al.

(10) Patent No.: US 9,980,698 B2
(45) Date of Patent: May 29, 2018

(54) RE-CALIBRATION OF PRE-RECORDED IMAGES DURING INTERVENTIONS USING A NEEDLE DEVICE

(75) Inventors: Levinus Pieter Bakker, Shanghai (CN); Bernardus Hendrikus Wilhelmus Hendriks, Eindhoven (NL); Adrian Emmanuel Desjardins, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 517 days.

(21) Appl. No.: 13/321,189

(22) PCT Filed: May 7, 2010

(86) PCT No.: PCT/IB2010/052030
§ 371 (c)(1),
(2), (4) Date: Nov. 18, 2011

(87) PCT Pub. No.: WO2010/136922
PCT Pub. Date: Dec. 2, 2010

(65) Prior Publication Data
US 2012/0059251 A1    Mar. 8, 2012

(30) Foreign Application Priority Data
May 28, 2009  (EP) ..................................... 09161321

(51) Int. Cl.
*A61B 19/00*     (2006.01)
*G06T 7/00*      (2006.01)
(Continued)

(52) U.S. Cl.
CPC .......... *A61B 8/0841* (2013.01); *A61B 5/0062* (2013.01); *A61B 5/0084* (2013.01);
(Continued)

(58) Field of Classification Search
CPC ... A61B 8/0841; A61B 5/0062; A61B 5/0066; A61B 5/0068; A61B 5/0071;
(Continued)

(56) References Cited

U.S. PATENT DOCUMENTS 5,207,673 A * 5/1993 Ebling et al. .................. 606/16
7,874,987 B2   1/2011 Altmann et al.
(Continued)

FOREIGN PATENT DOCUMENTS

JP     2002209870 A  *  7/2002
JP     2005106507 A     4/2005
(Continued)

OTHER PUBLICATIONS

By S Yamaguchi et al., "Real-Time Image Overlay System for Endoscopic Surgery Using Direct Calibration of Endoscopic Camera" Cars 2005, 1281, May 2005, pp. 756-761, Criteria: 1 Highlighted portions of cars.pdf (Abstract) (Real-time image overlay by world to endoscopic image transformation).

*Primary Examiner* — Michael Kahelin
*Assistant Examiner* — Helene Bor

(57) ABSTRACT

Re-calibration of pre-recorded images during interventions uses an interventional system including an imaging device providing images of an object, a needle device, and a processing device. The needle device includes a sensor for providing data corresponding to tissue properties. The processing device is configured to perform an overlay registration of pre-recorded images and live images provided by the imaging device, utilizing the data from the sensor. Thus, the accuracy of an overlay of images is increased.

20 Claims, 8 Drawing Sheets

(51) Int. Cl.
| | |
|---|---|
| *A61B 5/00* | (2006.01) |
| *A61B 6/12* | (2006.01) |
| *A61B 8/08* | (2006.01) |
| *A61B 6/00* | (2006.01) |
| *A61B 17/34* | (2006.01) |
| *A61B 8/00* | (2006.01) |
| *A61B 90/00* | (2016.01) |

(52) U.S. Cl.
CPC .............. *A61B 5/6848* (2013.01); *A61B 6/12* (2013.01); *A61B 6/5247* (2013.01); *A61B 8/5238* (2013.01); *A61B 17/34* (2013.01); *A61B 17/3403* (2013.01); *A61B 17/3417* (2013.01); *A61B 5/0066* (2013.01); *A61B 5/0068* (2013.01); *A61B 5/0071* (2013.01); *A61B 5/0073* (2013.01); *A61B 5/0075* (2013.01); *A61B 8/00* (2013.01); *A61B 2090/3614* (2016.02); *A61B 2090/374* (2016.02); *A61B 2090/376* (2016.02); *A61B 2090/378* (2016.02); *A61B 2090/3784* (2016.02)

(58) Field of Classification Search
CPC ... A61B 5/0073; A61B 5/0075; A61B 5/0084; A61B 5/6848; A61B 6/12; A61B 6/5247; A61B 8/00; A61B 8/5238; A61B 17/34; A61B 17/3403; A61B 17/3417; A61B 2019/5217; A61B 2019/5236; A61B 2019/5238; A61B 2019/5276; A61B 2019/528

USPC ...................... 604/164.12; 600/407; 382/131
See application file for complete search history.

(56) References Cited

U.S. PATENT DOCUMENTS

| | | | |
|---|---|---|---|
| 7,930,014 | B2 | 4/2011 | Huennekens et al. |
| 8,298,147 | B2 | 10/2012 | Huennekens et al. |
| 8,509,511 | B2 | 8/2013 | Sakaguchi |
| 8,750,964 | B2 | 6/2014 | Maschke |
| 2002/0115931 | A1* | 8/2002 | Strauss et al. ................ 600/420 |
| 2006/0241450 | A1* | 10/2006 | Da Silva et al. ............. 600/443 |
| 2007/0038061 | A1* | 2/2007 | Huennekens et al. ........ 600/407 |
| 2007/0118100 | A1 | 5/2007 | Mahesh et al. |
| 2007/0238997 | A1* | 10/2007 | Camus .......................... 600/437 |
| 2008/0095421 | A1 | 4/2008 | Sun et al. |
| 2009/0242776 | A1* | 10/2009 | Kobashi ................ A61B 6/541 250/363.04 |
| 2010/0331782 | A1* | 12/2010 | Hendriks et al. ........ 604/164.12 |

FOREIGN PATENT DOCUMENTS

| | | |
|---|---|---|
| WO | 2004019799 A2 | 3/2004 |
| WO | 2004019799R6 A2 | 3/2004 |
| WO | 2007135609 A2 | 11/2007 |
| WO | 2008111070 A2 | 9/2008 |

* cited by examiner

RE-CALIBRATION OF PRE-RECORDED IMAGES DURING INTERVENTIONS USING A NEEDLE DEVICE

FIELD OF THE INVENTION

The present invention relates to an interventional system including an image device and a needle device. Further, the invention relates to a method of combining pre-recorded images with live images of an object of interest. Particularly, the invention relates to a system and a method for providing a re-calibration of an overlay of pre-recorded images and live images.

BACKGROUND OF THE INVENTION

During an intervention, an interventionalist may use pre-recorded images and live imaging to navigate a medical device as a needle to an intended location. Prior to the intervention, a detailed image of the body is taken. This image is often three-dimensional. The coordinate system of this three-dimensional image is coupled to the location of the table and/or the medical imaging equipment that is being used during the intervention. In this way, an overlay of the live images that are being taken during the intervention and the pre-recorded image can be made. The accuracy of the overlay depends obviously on the accuracy of the coordinate system and for instance the accuracy of the position of the table and the live imaging equipment. More importantly, the overlay accuracy also depends on the movement of the patient, for instance due to breathing. For some interventions, as for instance biopsies of small sized deep seated lesions, the accuracy of the overlay is not sufficient.

SUMMARY OF THE INVENTION

It is an object of the invention to provide an interventional system and method of combining images, wherein the accuracy of an overlay of images is increased.

In general, this is achieved by using local tissue information. Such information may be provided by a so called photonic needle, i.e. by a needle device including optical fiber. The optical fiber may represent a sensor by means of which the needle device may detect features of tissue. Such features may also be detectable in the images to be combined.

Therefore, the essential feature of the invention is that the information of the sensor of the needle device will be combined with the information as provided by the live and pre-recorded images to enhance the overlay accuracy between pre-recorded and live images, by re-calibrating the coordinate system of the pre-recorded image with the coordinate system of a live image utilizing features that the sensor of the needle device detects, wherein these features are present in the pre-recorded images and more or less present in the live images.

To perform the overlay registration, a coordinate system or landmark in each of the images an overlay of which should be performed, is identified. In some instances a live image will not show all the details of a pre-recorded image. At this, the sensor of the needle device the position of which is locatable in the live image, provides additional information about the tissue at the location of the sensor. This additional information will be used to provide a better identification of the coordinate system or landmark in the live image, wherein this coordinate system or landmark may also be identifiable in the pre-recorded image so that the accuracy of the overlay may be improved by the system according to the invention.

In other words, given the specific tissue type that is recognized by the needle at a certain moment, combined with the rough knowledge of its position, the tissue volume under analysis can be exactly located in the coordinate system of the pre-recorded, i.e. pre-operative image, because tissue information is also available from the pre-recorded image. Given the spatial relation between this tissue volume and the needle, combined with the knowledge of the needle position in the live images, the position of this tissue volume can be determined with respect to the coordinate system of the live images as well. In this way, since the tissue location is known in the coordinate system of the pre-operative image and in the coordinate system of the live images, a re-calibration of the overlay registration can be done.

The above mentioned object is solved by the subject matter of the respective independent claims. Further exemplary embodiments are described in the respective depend claims.

Generally, an interventional system according to the invention comprises an imaging device providing images of an object, a needle device, and a processing device. The needle device comprises a sensor for providing data corresponding to tissue properties. The processing device is adapted to perform an overlay registration of pre-recorded images and live images provided by the imaging device, utilizing the data from the sensor.

According to another embodiment, the interventional system may further comprise an analyzing device, wherein the analyzing device may be coupled to the sensor and may be adapted to process the data from the sensor, thereby generating information about tissue properties.

The sensor of the needle device may comprise an optical fiber capable of emitting and receiving of light. The analyzing device may comprise a console for spectroscopy, wherein the console and the optical fiber may be connected to each other.

The console for spectroscopy may be adapted to provide information from one of the group consisting of reflectance spectroscopy, fluorescence spectroscopy, autofluorescence spectroscopy, differential path length spectroscopy, Raman spectroscopy, optical coherence tomography, light scattering spectroscopy, and multi-photon fluorescence spectroscopy.

Furthermore, the sensor of the needle device may comprise elements of a microscopic imaging capability. Such elements may include an optical fiber, a bundle of optical fibers, a lens and an actuation means. The actuation means may displace the optical fiber(s) together with the lens, or may displace only the fiber(s) or the lens. The imaging capability may also be realized just with a bundle of fibers and a lens, without an actuation means. With such an imaging capability, it may be possible to form microscopic images of the tissue in front of the needle device.

According to yet another embodiment, the imaging device may be a non-invasive imaging modality being one of the group consisting of an X-ray device, a computer tomography device, a magnet resonance tomography device, and an ultrasound device.

It should be noted that the needle device may comprise a structure and material capable to be visualized by the imaging device.

In other words, an integrated system according to the invention comprises a non-invasive imaging modality that can image the inside of the body, a needle device including a sensor including at least one fiber, the fiber being connected to a console capable of probing the tissue in front of or near the tip of the needle device. The non-invasive imaging modality can image the needle device inside the body, allowing coarse guidance of the needle device based on the non-invasive imaging modality. The optical modality is used to fine position the tip portion of the needle device in the targeted tissue. Preferably, the optical information is registered into the image of the non-invasive imaging modality. Preferably, in case the non-invasive imaging modality allows 3-dimensional imaging, the optical information is registered in the 3-dimensional coordinate frame of the image.

It is noted that the needle device might be, on the one hand, a biopsy needle, a cannula, or a trocar or, on the other hand, might also be a catheter adapted to receive a needle by which for example a biopsy will be actually performed.

The "tissue" investigated by the system may comprise all kind of living or dead tissue, e.g. human tissue, particularly epithelium-tissue (e.g. surface of the skin and inner lining of digestive tract), connective tissue (e.g. blood, bone tissue), muscle tissue and nervous tissue (e.g. brain, spinal cord and peripheral nervous system). "Tissue" may further comprise food products, biomaterials, synthetic materials, fluid or viscous substances, etc.

According to another aspect of the invention, a method of combining pre-recorded images with live images of an object of interest comprises the steps of making an overlay of pre-recorded images and live images, acquiring local tissue information, re-calibrate the overlay of the images utilizing the acquired local tissue information.

According to an embodiment, the method may further comprise the steps of receiving pre-recorded images from a data base, and receiving live images from an imaging device. The local tissue information may be acquired by means of a needle device.

According to another embodiment, the method step of making an overlay may include defining a coordinate system in a pre-recorded image and identifying a corresponding coordinate system in a live image or vice versa.

According to another embodiment, the method step of re-calibrating the overlay may include identifying structures in the pre-recorded image that correspond to the acquired information.

The pre-recorded images, the live images and the local tissue information may be real-time processed to calculate an error in the overlay.

The invention relates also to a computer program for a processing device, such that the method according to the invention might be executed on an appropriate system. The computer program is preferably loaded into a working memory of a data processor. The data processor is thus equipped to carry out the method of the invention. Further, the invention relates to a computer readable medium, such as a CD-Rom, at which the computer program may be stored. However, the computer program may also be presented over a network like the worldwide web and can be downloaded into the working memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted in different figures, similar elements are provided with the same reference signs.

DETAILED DESCRIPTION OF EXEMPLARY EMBODIMENTS

Figure 1:
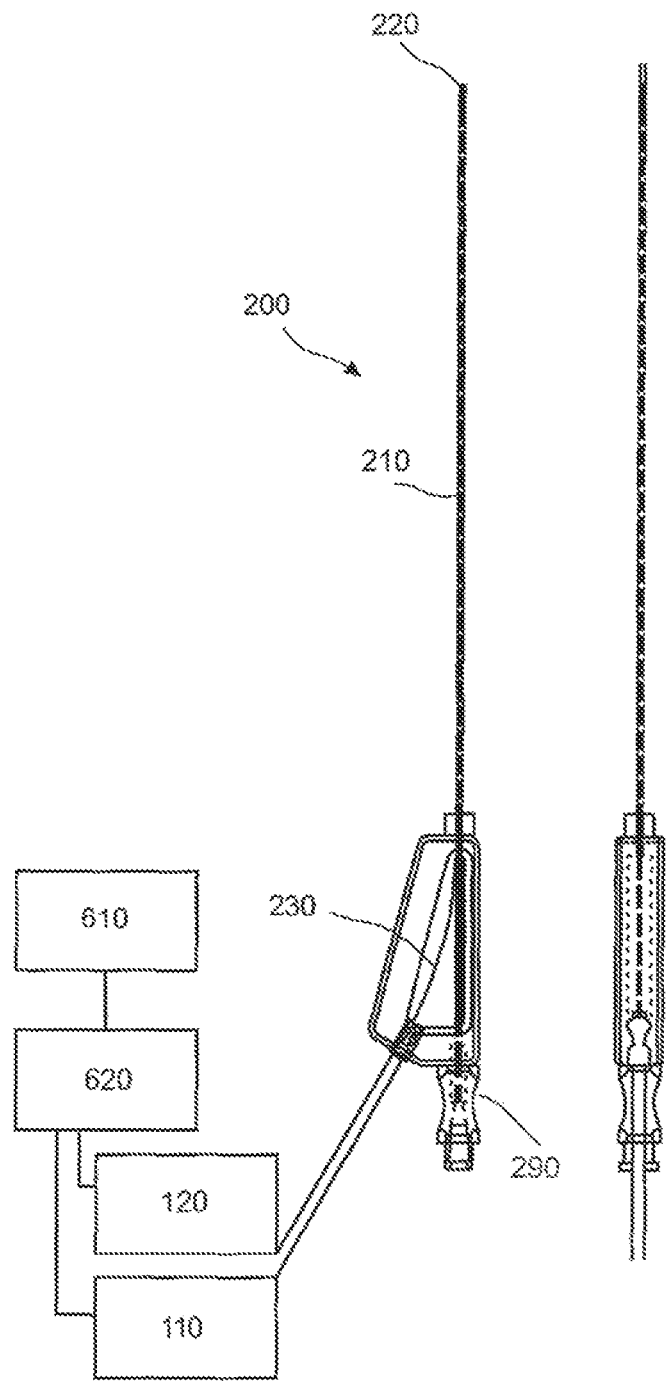
FIG. 1 shows a needle device according to the invention, including sensor modalities.

As illustrated in FIG. 1, a needle device 200 as part of a system according to an embodiment of the invention, comprises a shaft 210, a bevel at the tip portion of the shaft, at least one fiber 230, and a holder part 290.

For example, the shaft may have a length of 150 mm and a diameter of 1.3 mm. Further, the bevel may enclose an angle with the shaft axis of 20°. With the mentioned dimensions, it is intended to provide an order of magnitude and relations for a needle for tissue inspection based on optical spectroscopy.

In this embodiment, the fiber 230 which runs from the distal end, i.e. the surface of the bevel, through the shaft 210 to the holder part 290, passes through an opening of the holder part 290 out of the needle.

Furthermore, in FIG. 1 are schematically illustrated the elements of a system according to the invention. The system includes the needle device 200, a light source 110, a light detector 120, a processing unit 620 and a monitor 610. The processing unit 620 is capable of controlling the light source 110 to emit light into the fiber 230 such that light will be emitted through the distal end surface of the fiber 230 at the top of the bevel into surrounding tissue.

Depending on what kind of tissue is in front of the bevel, more or less of the emitted light will be reflected in the direction of the bottom of the bevel, to be received by another fiber. Through said other fiber, the light will be led to the light detector 120, which detector is adapted to transform the light into electrical signals. These electrical signals will be sent by, for example, wire to the processing unit 620. The processing unit will process the data corresponding to the electrical signals, so that the processed data might be visualized on a monitor 610. Based on said visualized data, it might be possible to diagnose whether a special type of tissue is in front of the tip portion of the needle 200.

It should be noted that also a subset of fibers consisting of a plurality of fibers, may be used to direct light into the tissue, while another subset of fibers is used to collect the light emanating from the tissue in which the needle is located.

The ratio of incident light versus outgoing light is defined as the reflectance. By illuminating the tissue with white light, and by spectrally resolving the detected light, a reflectance spectrum of the tissue can be obtained.

The reflectance spectra of different types of tissue are in general different due to the different molecular constitution of the tissues. As a result of measuring these spectra, it may be possible to identify different tissues from each other. The fact that the optical method has only a limited penetration depth (the imaging depth is only a few millimeters up to a few centimeters), guiding the needle or cannula without the guidance of the non-invasive modality is difficult because there is no overview where the needle or cannula is in space.

By proper feature extraction, this information on the tissue can be used to classify the tissue in different tissue types. This information can be used to properly place the needle at the correct location in the body.

Figure 2:
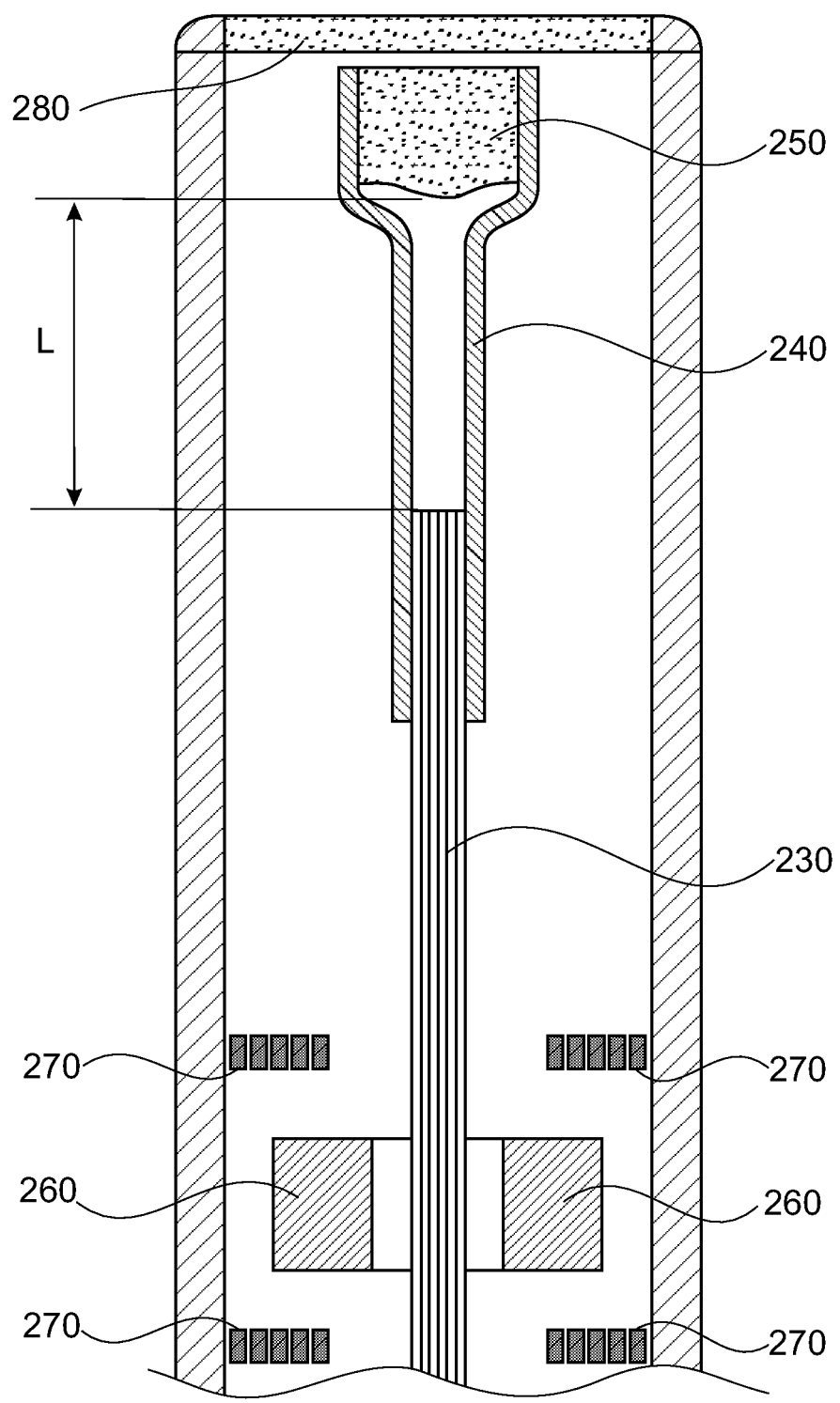
FIG. 2 shows a detail view of the tip portion of a needle device including a lens system of a sensor, according to an exemplary embodiment of the needle device.

FIG. 2 is a schematic cross-sectional drawing of an exemplary embodiment of the needle device, according to which a sensor 220 is realized by a lens system having a lens 250 and an actuation system 260, 270.

In order to have a compact lens system an aspherical surface of the lens 250 is applied. By making the lens 250 in an appropriate polymer, a compact lens system can be designed suitable for mass production. Preferably, the polymer should be a low density polymer to provide easy displacement of the lens system.

The lens system is positioned a distance L away from the optical exit of the optical fiber 230 as defined by the mount 240. The distance (L) is significantly larger than a core diameter of the optical fiber 230.

The lens system may be part mounted in the shaft 210 of the needle device together with an actuation system including an electromechanical motor system with coils 270 that are cooperating with magnets 260, the magnets being mechanically attached to the optical fiber 230 so as to perform scanning with the optical fiber 230 and the lens 250 by action of the motor system, wherein both an actuation of the optical fiber alone and an actuation of the optical fiber together with the lens is possible.

In this exemplary embodiment, the lens 250 is a single Plano-aspheric lens in front a thin flat exit window glass plate 280 as evident in FIG. 2. The aspheric lens is made of PMMA and has entrance pupil diameter of 0.82 mm. The numerical aperture (NA) is 0.67 and the focal length (measured in air) is 0.678 mm. The lens system is optimized for wavelength of 780 nm. The exit window 280 is flat and has no optical power.

It is noted, that the free working distance of the objective lens 250 must be larger than the exit window 280 thickness. The objective lens 250 will be scanned in front of the exit window. The exit window must have a certain thickness to be robust. Typically, the thickness is larger than 0.1 mm.

This embodiment is particularly, but not exclusively, advantageous for obtaining an improved optical sensor, particularly suited for miniature applications e.g. for in-vivo medical application. By attaching or mounting the lens system firmly to the optical fiber, the field of view of the optical sensor may be determined directly by the transverse stroke of the optical fiber. Hence only a relatively small stroke is required. The field of view is thus effectively no longer limited by the stroke. Because the lens system itself is only used for imaging close to the optical axis (i.e. small field of view), it may allow for simpler (i.e. less complex and thus fewer lens elements) optical designs that eases manufacturing while still having high image resolution.

It should further be mentioned that the optical sensor is particularly suited for relative simple and large-scale manufacturing because of the lens system being displaceably mounted on the end portion optical fiber. From a practical point of view, this may reduce the needed precision during manufacturing which, in turn, may lower the unit-price per probe. This is especially important because an endoscope, a catheter or needle with the optical sensor embedded will usually be disposed after a single use due to sanitary requirements.

Figure 3:
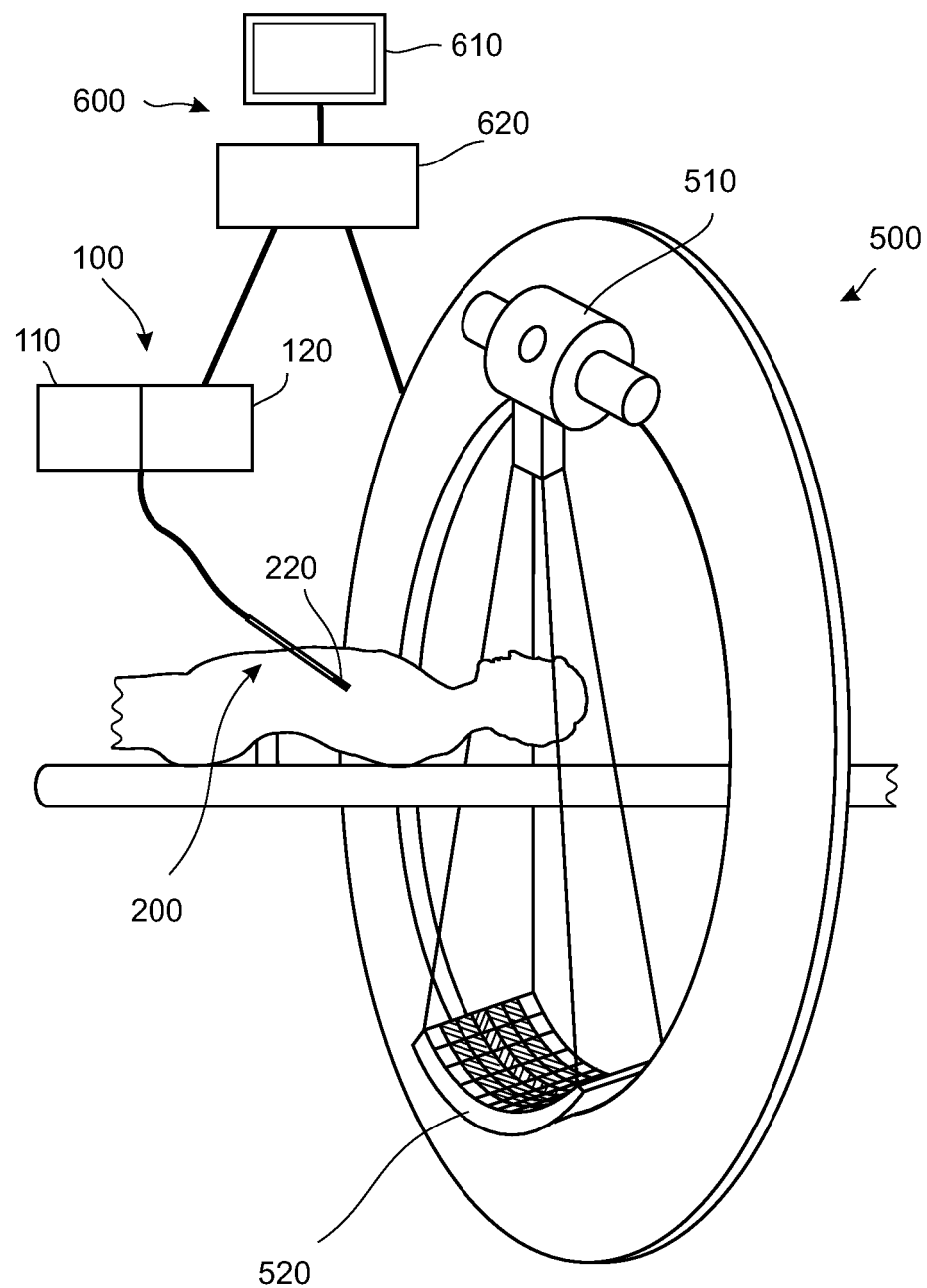
FIG. 3 shows an interventional system according to the invention.

FIG. 3 shows an interventional system according to an exemplary embodiment of the invention. The system comprises an elongated needle device 200, a sensor 220 which is located at the tip portion of the needle device, an imaging device 500 for assisting the coarse guidance, an analyzing device 100 for assisting the fine guidance, and a computing device 600. The analyzing device includes a light source 110 and a spectrograph as a light detector 120. The imaging device 500 includes a radiation source 510 and a detector array 520. The computing device includes a processor unit 620 for processing the signals coming from the imaging device 500 and from the analyzing device 100, and a monitor 610 for monitoring information for assisting the guidance of the biopsy device in a body.

As illustrated in FIG. 3, the interventional system comprises an image guided X-ray based needle guidance system 500 and a needle device 200 comprising a sensor, i.e. an optical fiber, which is connected with an analyzing device 100. The image guided needle navigation system provides integrated 2D/3D lesion imaging and an interactive image guided needle advancement monitoring, all of which is coupled to the optical information obtained by the needle, wherein the X-ray system 500 provides the coarse guidance, while the optical information received from the analyzing device 100, provides the final precise guidance to the device location.

The system is able to interactively follow the needle device from the incision to the target point by superimposing 2D fluoroscopic images on 3D tissue reconstruction and provide molecular tissue information at every point along the needle trajectory that is registered to the position inside the body of the patient. The region along the needle trajectory can be scanned (scan forward and scan aside) in order to provide indications on lesion existence at the molecular level. Preferably in reconstructing what tissue is in front of the needle the X-ray data and the position information of the needle is actively used in the optical reconstruction of what tissue is in front of the needle.

For example, tumor boundaries deduced from needle scanning and from the X-ray are compared. The X-ray information gives an estimate of the shape of the tumor, but the exact boundary cannot be determined. The photonic needle gives detailed information of the tumor boundary but this information is only obtained along the needle trajectory. Combining the X-ray shape of the tumor with the one dimensional information of the needle a new estimate of the 3D tumor size can be calculated. The newly deduced enlarged boundary will be a better estimate for the tumor boundary. X-ray and photonic needle information is further coupled to MRI images of the same area (MR data sets can be registered with the data sets produced by the X-ray machine). The needle device equipped with an optical fiber may also be used, for example, to position a localization wire. The localization wire containing fixation means and may also be equipped with a fiber.

Another aspect of making the information from the sensor at the needle device usable for the invention is that in translating the measured optical data into a tissue type can be difficult when no information about the surrounding morphology is known. Hence the decision making of the tissue characterization improves having the morphology information coming from the non-invasive imaging system as input. Hence preferably first the optical data is registered to the non-invasive imaging data, then the optical information together with the morphology information around the needle coming from the non-invasive imaging modality is used in translating the measured optical data into a tissue type in front of or near the needle. For instance when the needle is in soft tissue the optical information can be affected whether a bone structure is close by or not. Taking this into account a more reliable tissue characterization is possible.

To demonstrate the invention an experimental needle intervention will be described. A phantom, i.e. the object from which a biopsy should be taken, is placed on, for example, a C-arm bed and the needle is mounted on a stepper motor that moves the needle in the axial direction (minimal steps of 0.25 micron). The needle is connected with optical fibers to a spectrometer. At least one of the fibers detects light reflected from the tissue, hence is an optical element.

The needle intervention consists of acquiring X-ray and fluoroscopic X-ray images while in addition optical reflectance spectra are measured by the needle containing fibers coupled to a console that is connected to the X-ray system.

After a full rotation of the C-arm around the object, it is possible to generate 3D reconstructions of the object from the X-ray information, including the position of the needle. Furthermore, advancement of the needle can be done under fluoroscopy X-ray imaging. In parallel, tissue information is acquired by the needle.

Figure 4:
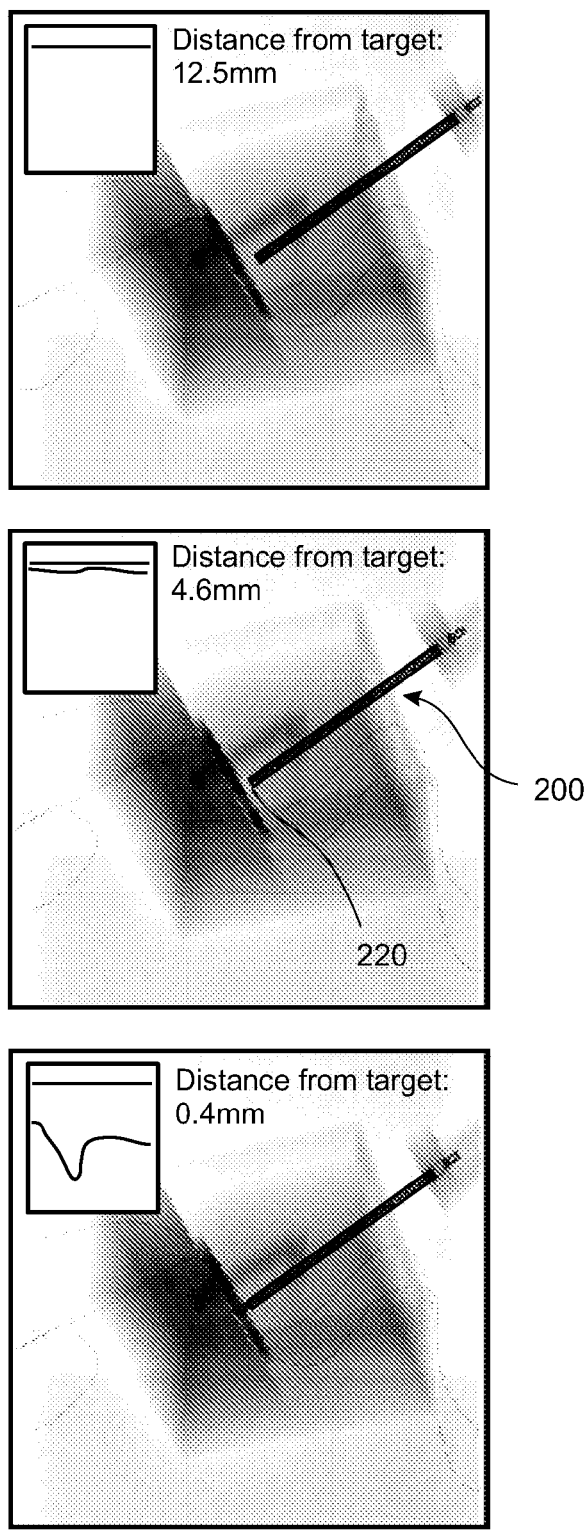
FIG. 4 illustrates examples of images showing a needle device in an object, wherein the tip of the needle device has different distances to a target structure.

FIG. 4 shows three illustrations which might be shown on a monitor to assist in guiding a needle device. Each illustration is mainly an image of an X-ray device, having added in the up left corner an illustration of the spectrum achieved by the analyze device on the basis of the tissue information from the needle. The fluoroscopy image of the X-ray device allows determining the relative position of the needle (elongated black line from the middle of each illustration to up right) with respect to the phantom (dark shadow), while the spectral information clearly shows when the small tube (black contrast line from up left to down right) is approached. It allows locating the needle within 100 micron accuracy. Although the information of the X-ray image and the optical information are exemplarily shown in a combined image, there are various other ways to present the combined information for instance by using colors.

As an example, consider a structure of which a detailed pre-recorded image is required. The same structure is imaged live by the imaging device (for instance fluoroscopy X-ray imaging). This provides a less detailed image and registering the pre-recorded image to this image can be done with a limited accuracy. By using the optical data (see inserts in FIG. 4), the position of the needle to the relevant features can be determined by higher accuracy. Registering the new acquired image to the pre-recorded data set can now be done with higher accuracy based on the information from the needle device.

Using the information from the sensor at the needle device may also provide for the possibility to start the needle progression right away without live guidance, just on the basis of a pre-recorded image. By using the local tissue information by the photonic needle, a physician may judge where the needle is located approximately in the pre-recorded image.

Figure 5:
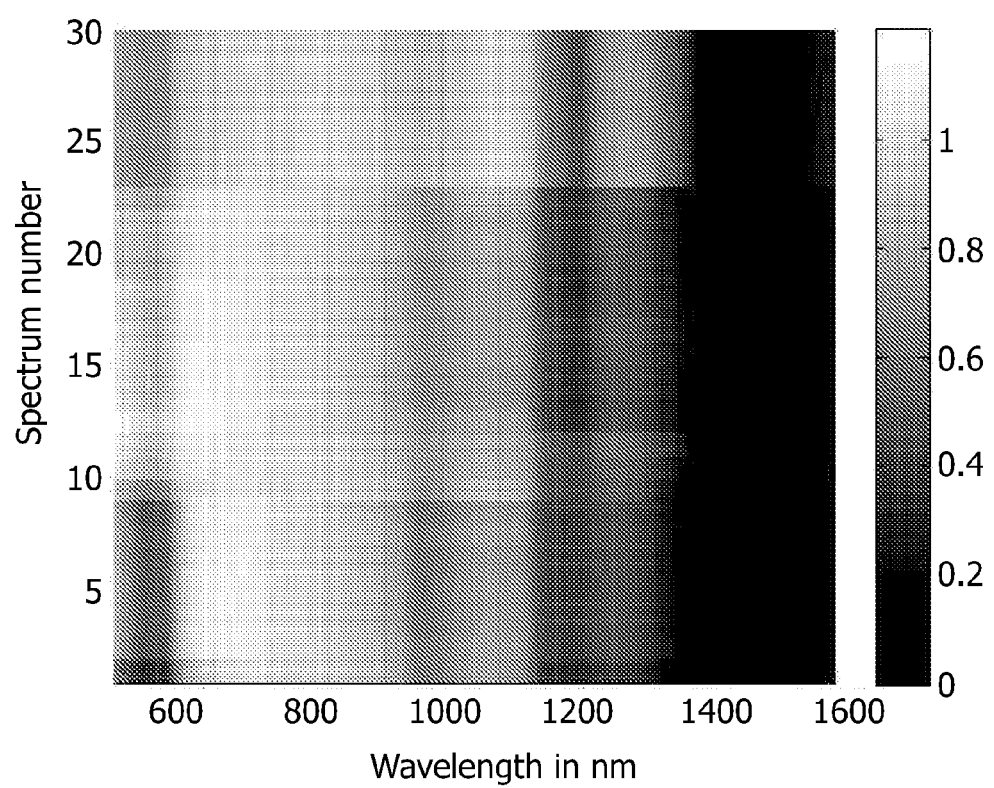
FIG. 5 is a first illustration of wavelengths for several spectra.
Figure 6:
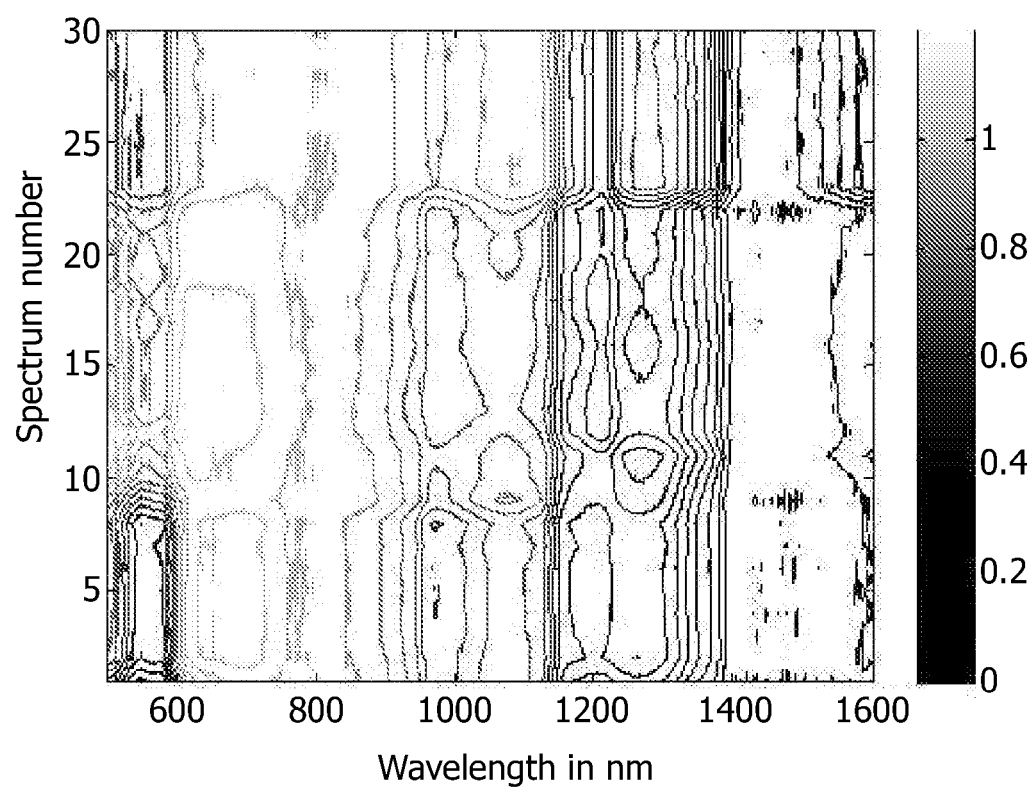
FIG. 6 is a second illustration of wavelengths for several spectra.
Figure 7:
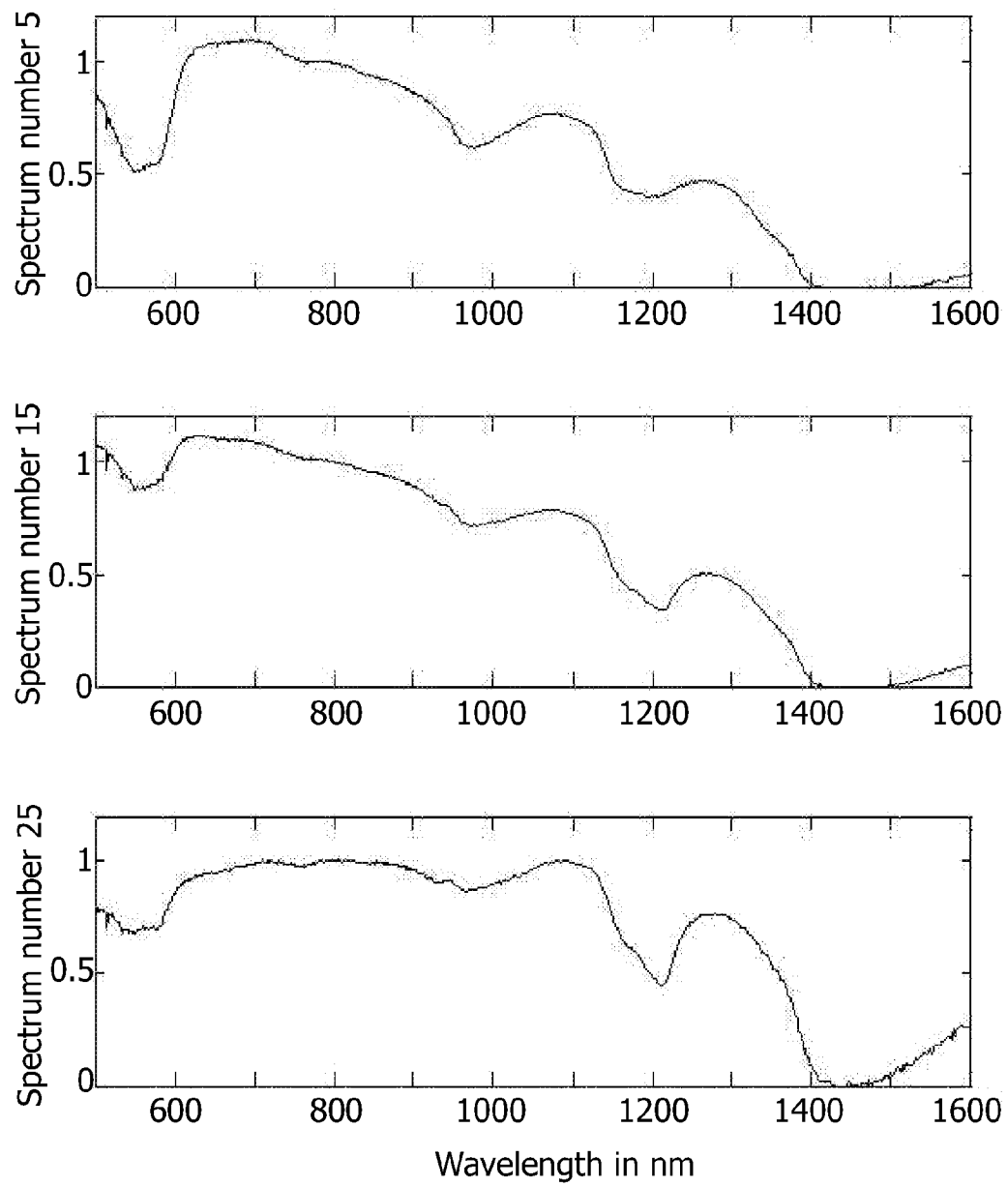
FIG. 7 is an illustration of wavelengths for three exemplary spectra.

FIGS. 5 to 7 show examples of acquired spectra during a needle intervention for different positions of the needle in tissue. The higher the spectrum number the further the needle is in the tissue.

In FIGS. 5 and 6 transitions may be clearly observed when going from one tissue type to another tissue type. In FIG. 7 the spectra for three different positions is illustrated. In this example the transitions are clear and also the spectra are sufficiently different for discriminating the transitions. These for instance soft tissue transitions may not be visible in the X-ray image. Therefore linking the X-ray image to a pre-recorded, for instance, MRI image showing these soft tissue transitions, these landmarks may not be used. With the optical information this now becomes possible.

Figure 8:
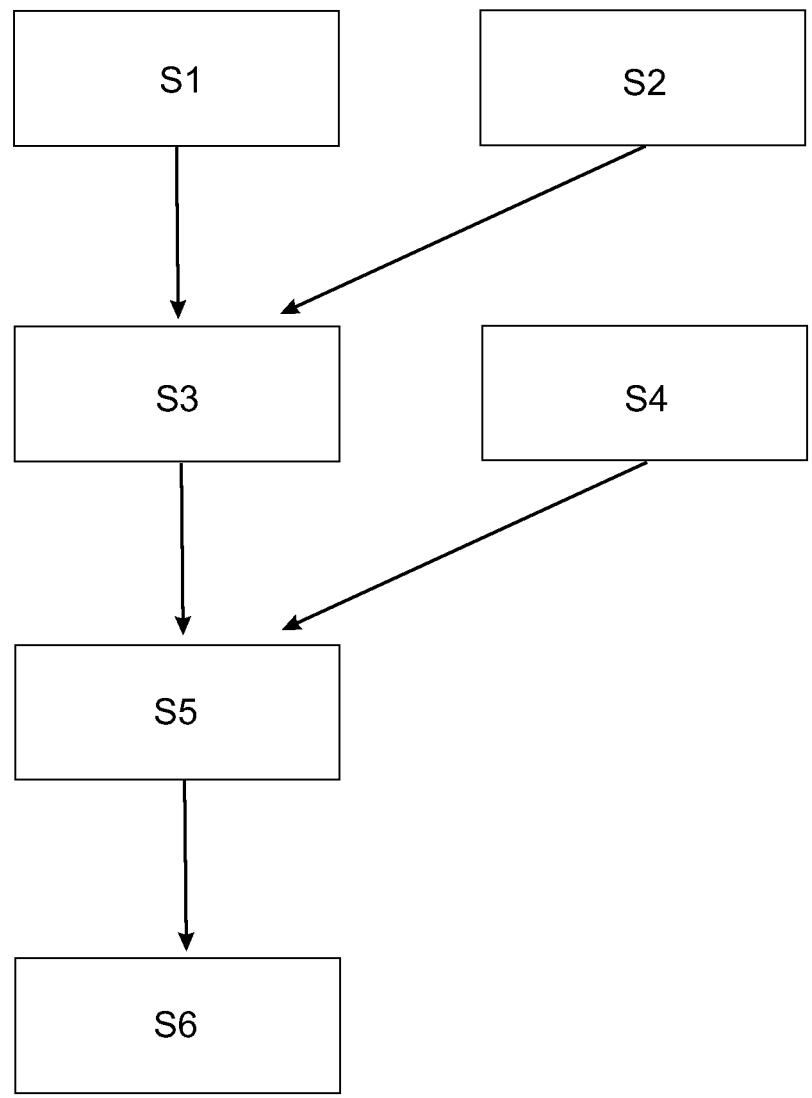
FIG. 8 is a flow chart of the method according to the invention.

FIG. 8 is a flow chart, showing the steps of a method of combining pre-recorded images with live images of an object of interest according to the invention. It will be understood, that the steps described with respect to the method, are major steps, wherein these major steps might be differentiated or divided into several sub steps. Furthermore, there might be also sub steps between these major steps. Therefore, a sub step is only mentioned, if said step is important for the understanding of the principles of the method according to the invention.

In step S1 of the method according to the invention, a pre-recorded image of the region of interest of the patient is measured and track of the coordinate system is kept.

In step S2, an intervention using live imaging is performed.

In step S3, an overlay of pre-recorded and live image is made.

Making an overlay may include the following sub-steps:

A feature detection step, in which salient and distinctive objects (closed-boundary regions, edges, contours, line intersections, corners, etc.) are manually or, preferably, automatically detected. For further processing, these features may be represented by their point representatives (centers of gravity, line endings, distinctive points), which are called control points.

A feature matching step, in which the correspondence between the features detected in the live image and those detected in the pre-recorded image is established. Various feature descriptors and similarity measures along with spatial relationships among the features are used for that purpose.

A transform model estimation step, in which the type and parameters of the so-called mapping functions, aligning the live image with the pre-recorded image, are estimated. The parameters of the mapping functions are computed by means of the established feature correspondence.

An image resampling and transformation step, in which the live image is transformed by means of the mapping functions. Image values in non-integer coordinates are computed by the appropriate interpolation technique.

In step S4 of the method according to the invention, local tissue information as a distinctive feature is acquired from a photonic needle.

In step S5, structures in the live image are identified within the sphere as defined by the overlay accuracy in the pre-recorded image that correspond to the information as provided by the photonic needle, as for instance a boundary between tissue types, or blood vessels, or other structures.

In step S6, the coordinate system of the pre-recorded image relative to the live image is re-calibrated in such a way that the structure as detected by the photonic needle is exactly at the tip of the needle in the pre-recorded image (obviously, the needle tip is visible in the live image).

While the invention has been illustrated and described in detail in the drawings and foregoing description, such illustration and description are to be considered illustrative or exemplary and. not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

List of Reference Signs
100 analyzing device
110 light source
120 light detector
200 needle device
210 shaft
220 sensor
230 fiber
240 mount
250 lens
260 magnet
270 coil
280 window
290 holder part
500 imaging device
510 radiation source
520 detector array
600 processing device
610 monitor
620 processing unit

The invention claimed is:

1. An interventional system, comprising:
an imaging device providing a live image of an object;
a needle device locatable near the object and having a position in the object which is locatable in the live image; and
a processing device configured to receive a pre-recorded image of he object from a database,
wherein the needle device comprises a sensor for providing local data corresponding to tissue properties in a vicinity of the sensor,
wherein the processing device configured to perform an overlay registration of the pre-recorded image and the live image, utilizing the local data from the sensor so that the overlay registration is re-calibrated utilizing the local data from the sensor to form a final image based on the pre-recorded image, the live image and the local data from the sensor, and
wherein the processing device is further configured to display information on the final image, the information including an optical spectrum of the tissue properties determined from the local data by an analyzing device, and to determine a tissue type in the vicinity of the sensor based on the local data from the sensor including the optical spectrum and morphology information around the sensor obtained from the live image, the optical spectrum indicating a molecular constitution of the tissue.

2. The interventional system of claim 1, wherein the analyzing device is coupled to the sensor and is configured to process the local data for the sensor, thereby generating the information about the tissue properties.

3. The interventional system of claim 2, wherein the sensor of the needle device comprises an optical fiber configured to emit and receive light, and wherein the analyzing device comprises a console for spectroscopy, wherein the console and the optical fiber are connected to each other.

4. The interventional system of claim 3, wherein the console for spectroscopy comprises one of reflectance spectroscopy, fluorescence spectroscopy, autofluorescence spectroscopy, differential path length spectroscopy, Raman spectroscopy, optical coherence tomography, light scattering spectroscopy, and multi-photon fluorescence spectroscopy.

5. The interventional system of claim 2, wherein the sensor of the needle device comprises elements of a microscopic imaging capability.

6. The interventional system of claim 1, wherein the imaging device is a non-invasive imaging modality and comprises one of an X-ray device, a computer tomography device, a magnet resonance tomography device, and an ultrasound device.

7. The interventional system of claim 1, wherein the needle device comprises a structure and material capable to be visualized by the imaging device.

8. The interventional system of claim 1, wherein the processing device is further configured to calculate an error in the overlay in real-time by processing the pre-recorded image, the live image and the local data in real-time.

9. The interventional system of claim 1, wherein the sensor of the needle device comprises a lens, a mount and an optical fiber configured to emit and receive light through the lens, and wherein the mount is located between the lens and the optical fiber, the mount having a length which is larger than a core diameter of the optical fiber.

10. The interventional system of claim 1, wherein the optical spectrum is a reflectance spectrum determined based on a ratio of incident light on the object emitted by the sensor versus outgoing light from the object received by the sensor.

11. The interventional system of claim 1, wherein the optical spectrum is displayed in a separate window overlaid on the final image at a position away from an image of the needle device, and wherein the optical spectrum indicates when the needle device approaches the object and allows locating the needle device in the final image within 100 micron accuracy.

12. The interventional system of claim 1, wherein the needle device comprises an actuator, a lens, and an optical fiber configured to emit and receive light through the lens, and wherein the actuator is configured to displace one of he optical fiber together with the lens, only the optical fiber and only the lens.

13. The interventional system of claim 1, wherein the processing device is further configured:
estimate a shape of a tumor from the live image obtained by the imaging device;
obtain one dimensional information of a boundary of the tumor along a trajectory of the needle device;
combine the estimated shape with the one dimensional information to form a combined image; and
deduce an enlarged boundary from the combined image.

14. A method of combining a pre-recorded image with a live image of an object of interest, the method comprising the acts of:
receiving the pre-recorded image of the object of interest from a database;
generating the live image of the object of interest and a needle device near the object of interest by an imaging device;
generating an overlay of the pre-recorded image and the live image;
receiving local tissue information from the needle device located in a vicinity of the object of interest determined from the overlay, the local tissue information corresponding to tissue properties in the vicinity of the object of interest;
determining a tissue type in the vicinity of the object of interest based on the local tissue information from the needle device including the optical spectrum and morphology information around the needle device obtained from the live image;
re-calibrating the overlay of the images utilizing the received local tissue information to form a final image based on the pre-recorded image, the live image and the received local tissue information; and
displaying information on the final image, the information including an optical spectrum of the tissue properties determined from the local tissue information by an analyzing device, the optical spectrum indicating a molecular constitution of the tissue.

15. The method of claim 14, wherein the act of generating the overlay includes defining a coordinate system in the pre-recorded image and defining a corresponding coordinate system in the live image.

16. The method of claim 14, wherein the re-calibrating act includes identifying features in the live image that correspond to the received local tissue information.

17. The method of claim 14, wherein the pre-recorded image, the live image and the local tissue information are real-time processed to calculate an error in the overlay.

18. The method of claim 14, wherein the needle device comprises a sensor having a lens, a mount and an optical fiber configured to emit and receive light through the lens, and wherein the mount is located between the lens and the optical fiber, the mount having a length which is larger than a core diameter of the optical fiber.

19. The method of claim 14, wherein the optical spectrum is a reflectance spectrum determined based on a ratio of incident light on the object of interest emitted by a sensor of the needle device versus outgoing light from the object of interest received by the sensor.

20. A non-transitory computer readable medium comprising computer instructions which, when executed by a processor, configure the processor to perform the acts of:
receiving the pre-recorded image of the object from a database;
causing generation of a live image of the object obtained from an imaging device and a needle device near the object of interest;
generating an overlay of the pre-recorded image and the live image;
receiving local tissue information from the needle device located in a vicinity of the object determined from the overlay, the local tissue information corresponding to tissue properties in the vicinity of the object;
determine a tissue type in the vicinity of the object of interest based on the local tissue information from the needle device including the optical spectrum and morphology information around the needle device obtained from the live image;
re-calibrating the overlay of the images utilizing the received local tissue information to form a final image based on the pre-recorded image, the live image and the received local tissue information; and
causing display of information on the final image, the information including an optical spectrum of the tissue properties determined from the local tissue information by an analyzing device, the optical spectrum indicating a molecular constitution of the tissue.

* * * * *